(12) United States Patent
Liu et al.

(10) Patent No.: US 7,381,405 B2
(45) Date of Patent: Jun. 3, 2008

(54) METHODS OF PREPARING LYMPHOCYTES THAT EXPRESS INTERLEUKIN-2 AND THEIR USE IN THE TREATMENT OF CANCER

(75) Inventors: Ke Liu, Rockville, MD (US); Steven A. Rosenberg, Potomac, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 244 days.

(21) Appl. No.: 10/531,145

(22) PCT Filed: Oct. 15, 2002

(86) PCT No.: PCT/US02/33243

§ 371 (c)(1), (2), (4) Date: May 19, 2005

(87) PCT Pub. No.: WO2004/034789

PCT Pub. Date: Apr. 29, 2004

(65) Prior Publication Data

US 2005/0233451 A1    Oct. 20, 2005

(51) Int. Cl.
*A01N 63/00* (2006.01)
*A61K 39/00* (2006.01)
*C12N 15/00* (2006.01)
*C12N 15/63* (2006.01)
*C07H 21/04* (2006.01)

(52) U.S. Cl. .................. 424/93.21; 435/320.1; 435/325; 435/455; 536/23.5; 536/24.1; 424/184.1

(58) Field of Classification Search ............. 424/93.21, 424/184.1; 435/320.1, 325, 455; 536/23.5, 536/24.1
See application file for complete search history.

(56) References Cited

U.S. PATENT DOCUMENTS

| 5,662,896 | A | 9/1997 | Barber et al. |
|---|---|---|---|
| 5,681,562 | A | 10/1997 | Sobol et al. |
| 5,874,556 | A | 2/1999 | Lupton et al. |
| 6,310,045 | B1 | 10/2001 | Barber et al. |
| 6,312,957 | B1 * | 11/2001 | Einerhand et al. .......... 435/456 |
| 6,562,347 | B1 * | 5/2003 | Kwak et al. ............. 424/192.1 |
| 2002/0106799 | A1 | 8/2002 | Finer et al. |
| 2002/0119571 | A1 | 8/2002 | Ritter et al. |

OTHER PUBLICATIONS

Roifman, C. M., 2000, Pediatric Research, vol. 48, No. 1, p. 6-11.*
Hattori et al., 1990, The Journal of Immunology, vol. 144, No. 10, p. 3809-3815.*
Asami et al., 1996, European Journal of Haematology, vol. 57, p. 278-285.*
Trevor et al., *Cancer Immunol. Immunother.*, 50, 397-407 (2001).
Wang et al., *Exp. Opin. Biol. Ther.*, 1(2), 277-290 (2001).
Scholl et al., *J. of Immunotherapy*, 23(5), 570-580 (2000).
Liu et al., *J. Immunol.*, 167, 6356-6365 (Nov. 2001).
Liu et al., *Proc. Amer. Society Clin. Oncol.*, 38th Annual Mtg., Abst. No. 71, 19a (Apr. 2002).
Tan et al., *Anticancer Res.*, 16, 1993-1998 (Jul.-Aug. 1996).
Uckert et al., *Hum. Gene Ther.*, 11, 1005-1014 (May 2000).

* cited by examiner

*Primary Examiner*—Shin-Lin Chen
(74) *Attorney, Agent, or Firm*—Leydig, Voit & Mayer

(57) ABSTRACT

The invention provides methods of preparing autologous T-lymphocytes for re-introduction into a patient having cancer, which method comprises obtaining peripheral blood mononuclear cells (PBMCs) from a patient immunized with an antigen of the cancer, stimulating the PBMCs with the antigen of the cancer in vitro, transducing the PBMCs with a retroviral vector, which (a) comprises and expresses a human interleukin-2 (IL-2) coding sequence operably linked to a retroviral promoter, (b) does not comprise an exogenously introduced gene that enables phenotypic selection, and (c) comprises a viral envelope that efficiently transduces CD8+ T-lymphocytes; compositions comprising cells obtained in accordance with such methods; and methods of treating a patient having cancer by administering to the patient cells obtained in accordance with such methods or compositions comprising same.

13 Claims, No Drawings

METHODS OF PREPARING LYMPHOCYTES THAT EXPRESS INTERLEUKIN-2 AND THEIR USE IN THE TREATMENT OF CANCER

Incorporated by reference in its entirety herein is a computer-readable nucleotide/amino acid sequence listing submitted concurrently herewith and identified as follows: One 5,000 Byte ASCII (Text) file named "234872sequence.2.TXT," created on Aug. 20, 2007.

TECHNICAL FIELD OF THE INVENTION

The present invention relates to methods of preparing autologous T-lymphocytes and tumor-infiltrating lymphocytes that express interleukin-2 (IL-2) and related compositions and methods of use in the treatment of cancer.

BACKGROUND OF THE INVENTION

One major obstacle limiting the efficacy of adoptive T-cell transfer (adoptive immunotherapy) in the treatment of cancer patients is the short-term survival of the transferred cells. In-vitro-activated T-cells undergo apoptosis upon transfer in vivo. Accordingly, there remains a need for improved T-cells for adoptive immunotherapy. It is an object of the present invention to provide such T-cells. This and other objects and advantages of the present invention, as well as additional inventive features, will be apparent from the detailed description provided herein.

BRIEF SUMMARY OF THE INVENTION

The present invention provides a method of preparing autologous T-lymphocytes for re-introduction into a patient having cancer. The method comprises:
(i) obtaining peripheral blood mononuclear cells (PBMCs) from a patient immunized with an antigen of the cancer,
(ii) stimulating the PBMCs with the antigen of the cancer in vitro, and
(iii) transducing the PBMCs with a retroviral vector, which (a) comprises and expresses a human IL-2 coding sequence operably linked to a retroviral promoter, (b) does not comprise an exogenously introduced gene that enables phenotypic selection, and (c) comprises a viral envelope that efficiently transduces CD8+ T-lymphocytes, whereupon autologous T-lymphocytes are prepared for re-introduction into a patient having cancer.

A composition comprising T lymphocytes obtained in accordance with the above method is also provided. Seventy-five percent or more of the T-lymphocytes in the composition are CD8+, and the cells do not contain an exogenously introduced gene that enables phenotypic selection.

In view of the foregoing, the present invention provides a method of treating a patient having cancer. The method comprises administering to the patient autologous T-lymphocytes, which have been prepared in accordance with the above method, alone or in further combination with human IL-2 receptor α-chain, in amount(s) sufficient to treat the patient for cancer.

The present invention further provides a method of preparing autologous tumor-infiltrating lymphocytes (TILs) for re-introduction into a patient having cancer. The method comprises:
(i) obtaining TILs from a patient, who has been optionally immunized with an antigen of the cancer,
(ii) transducing the TILs, which have been optionally stimulated with the antigen of the cancer in vitro, with a retroviral vector, which (a) comprises and expresses a human IL-2 coding sequence operably linked to a retroviral promoter, (b) does not contain an exogenously introduced gene that enables phenotypic selection, and (c) comprises a viral envelope that efficiently transduces CD8+ TILs, whereupon autologous TILs are prepared for re-introduction into a patient having cancer.

A composition comprising TILs obtained in accordance with the above method is also provided. Seventy-five percent or more of the TILs are CD8+, and the cells do not contain an exogenously introduced gene that enables phenotypic selection.

In view of the foregoing, the present invention provides another method of treating a patient having cancer. The method comprises administering to the patient autologous TILs, which have been prepared in accordance with the above method, alone or in further combination with human IL-2 receptor α-chain, in amount(s) sufficient to treat the patient for cancer.

DETAILED DESCRIPTION OF THE INVENTION

The present invention is predicated on the discovery that anti-tumor T-lymphocytes can be genetically modified to make their proliferation IL-2-independent without malignant transformation and/or immortalization. In addition, by making the growth of the T-lymphocytes dependent on stimulation and by enabling the T-lymphocytes to self-select, the T-lymphocytes are particularly valuable in the adoptive immunotherapeutic treatment of cancer patients.

The present invention provides a method of preparing autologous T-lymphocytes or autologous TILs for re-introduction into a patient having cancer. The method comprises obtaining autologous T-lymphocytes or TILs from the patient. While any suitable source of T-lymphocytes can be used, PBMCs are a preferred source. Suitable sources of T-lymphocytes, such as PBMCs, and TILs can be isolated from the patient in accordance with methods known in the art.

Desirably, the patient, from whom the T-lymphocytes are obtained, has been immunized with an antigen of the cancer in accordance with methods known in the art (see, e.g., Rosenberg et at., Nat. Med. 4:321-327 (1998)). If TILs are obtained from the patient, the prior immunization of the patient with an antigen of the cancer is optional. Preferably, the antigen of the cancer is one that induces a strong immune response against the cancer in the patient. For example, if the cancer is melanoma, preferably the patient is immunized with gp100, more preferably amino acids 209-217 of gp100, and most preferably amino acids 209-217 of gp100 with a methionine substitution at position 210, referred to herein as the 209-2M peptide (SEQ ID NO: 5). Her-2/Neu is a preferred antigen for immunization of a patient to be treated for breast cancer. If the patient has prostate cancer, preferably the patient is immunized with prostate-specific antigen (PSA). A patient with colon cancer is preferably immunized with carcinoembryonic antigen (CEA). These antigens are exemplary and are not intended to be limiting.

Once a source of autologous T-lymphocytes has been obtained, the cells, such as PBMCs, are stimulated with the antigen of the cancer in vitro. If autologous TILs have been obtained, the in vitro stimulation of the TILs with the antigen of cancer is optional. The cells can be stimulated in vitro with the antigen of the cancer to be treated by any suitable manner. A preferred manner is exemplified in the Examples set forth herein. Desirably, the antigen used to stimulate the cells in vitro is the same antigen used to immunize the patient. "Stimulate," "stimulated," and "stimulation" are all used to refer to the phenomenon of the T-cell receptor complex binding to a stimulus, such as a specific stimulus, e.g., a cancer antigen, or a non-specific stimulus, e.g., an anti-CD3 antibody (OKT3, for example, which is available from Orthoclone, Ortho-biotech, Raritan, N.J.) or phytohemagglutinin (PHA), which results in cellular proliferation and the manifestation of anti-tumor activity.

After the cells, such as PBMCs, have been stimulated in vitro with the antigen of the cancer to be treated, the cells are transduced with a retroviral vector, which comprises and expresses a human IL-2 coding sequence operably linked to a retroviral promoter, i.e., the retroviral 5' long terminal repeat (LTR) promoter, and which comprises a viral envelope that efficiently transduces CD8+ T-lymphocytes. The coding sequence of a human IL-2 is available (see, e.g., Liu et al., J. Immunol. 167: 6356-6365 (2001)). The operable linkage of a coding sequence, such as that which encodes human IL-2, and a retroviral promoter is within the ordinary skill in the art. See, e.g., Sambrook and Russell, *Molecular Cloning,* 3rd Ed., SCHL Press (2001). If it is desired to increase the expression of IL-2, the retroviral promoter can be replaced with a stronger promoter, such as the cytomegaloviral (CMV) promoter, such as in the context of a CMMP retroviral construct (Klein et al., J. Exp. Med. 191: 1699-1709 (2000)).

The retroviral vector must comprise a viral envelope that efficiently transduces CD8+ T-lymphocytes. A preferred viral envelope is that of gibbon ape leukemia virus (GALV), which can be provided by the packaging cell line PG13. Alternatively, the retroviral vector can be packaged in the cell line PA317.

Transduction of cells with retroviral vectors is within the skill in the art. See, e.g., Sambrook (2001), supra. The culture of PBMCs, TILs and transduced PBMCs and TILs is also within the skill in the art. See, e.g., the Examples herein. Although IL-2-independent for their growth, IL-2-transduced PBMC self-regulate their growth by down-regulation of the expression of the transduced IL-2 gene. IL-2-transduced CD8+ TILs can secrete IL-2 upon tumor antigen stimulation, can proliferate in the absence of exogenous IL-2 after the destruction of autologous tumor cells, without the help of CD4+ cells, and can self-select for their growth in the absence of added IL-2.

If desired, the retroviral vector can further comprise and express a human IL-2 receptor α-chain (otherwise referred to as CD25 or Tac) coding sequence. The coding sequence of a human IL-2 receptor α-chain is available (see, e.g., Waldmann, J. of Biol. Chem. 266: 2681-2684 (1991)). The coding sequence of a human IL-2 receptor α-chain can be operably linked to a retroviral promoter as described above. Alternatively, a separate vector comprising and expressing a human IL-2 receptor α-chain coding sequence can be introduced into the cell. While any suitable vector can be used and any suitable vector can be operably linked to the IL-2 receptor α-chain coding sequence as appropriate for the vector of choice, desirably the vector does not adversely affect the efficient transduction of CD8+ T-lymphocytes with the retroviral vector comprising and expressing a human IL-2 and does not adversely affect the expression of IL-2 therein. If a separate vector is used to express a human IL-2 receptor α-chain, preferably the vector is a retroviral vector, such as GALV, and the IL-2 receptor α-chain coding sequence is operably linked to a retroviral promoter.

In view of the foregoing, the present invention further provides a composition comprising T-lymphocytes or TILs obtained in accordance with the above methods. Desirably, 75% or more of the T-lymphocytes or TILs are CD8+, the cells do not contain an exogenously introduced gene that enables phenotypic selection, and the composition is suitable for re-introduction into the patient from whom the T-lymphocytes were obtained. As such, the composition can contain various other components as known in the pharmaceutical arts. See, e.g., *Remington's Pharmaceutical Sciences,* 17th ed., (Mack Publishing Company, Philadelphia, Pa.: 1985).

Also in view of the foregoing, the present invention provides a method of treating a patient having cancer. The method comprises administering to the patient autologous T-lymphocytes or TILs, which have been prepared in accordance with the above methods. The autologous T-lymphocytes or TILs can be administered by any suitable route as known in the art. The T-lymphocytes or TILs preferably are administered intravenously, although the T-lymphocytes or TILs can be administered intra-arterially. Preferably, $3 \times 10^{11}$ autologous T-lymphocytes or TILs are administered as a single dose. If necessary, a second dose can be administered after about 6-8 weeks.

The method can further comprise the administration of human IL-2 receptor α-chain, whether encoded in the vector encoding human IL-2, or encoded in a separate vector for introduction into the T-lymphocytes or TILs. When the cells are no longer stimulated by cancer antigen, such as when there no longer are any cancer cells present, the IL-2-transduced T-lymphocytes or TILs stop growing and eventually ere eliminated.

EXAMPLES

The following examples are intended to illustrate the present invention and are not intended to limit its scope in any way.

The follow materials were used in the examples:
Ca++– Mg++–, Phenol red-free Hanks' balanced salt solution (HBSS) (BioWhittaker)
RPMI 1640 with L-Glutamine (BioWhittaker)
HEPES, 1 M, pH 7.0, stock (BioWhittaker)
2-Mercaptoethanol, $5.5 \times 10^{-2}$ M in D-PBS, stock (Gibco BRL)
Penicillin G sodium (10,000 units/ml), streptomycin (10,000 mg/ml) stock
(BioWhittaker). Omit if patient is allergic to Penicillin.
Gentamycin (50 mg/ml) stock (BioFluids). Omit if patient is allergic to Gentamycin.
Ciprofloxacin (Cipro 1% solution, Bayer). Omit if patient is allergic to Ciprofloxacin.
Fungizone (250 mcg/ml stock; Biofluids). Omit if patient is allergic to Fungizone.
Aim V serum free lymphocyte growth medium (Gibco)
0.9% sodium chloride, USP (Baxter)
Human Serum, type AB (Valley Biomedical)
Human PBMCs
Human albumin (Plasbumin-25, Bayer))
Recombinant human IL-2 ($10^6$ CU/ml) (Cetus Oncology Div, Chiron*)
OKT3 (Ortho-anti-CD3) (Orthoclone)
g209-2M peptide 1.0 mg/ml stock (Multiple Peptide Systems)

Lymphocyte separation medium (LSM) (ICN)
96-well tissue culture plates, flat-bottom and U-bottom (Costar)
Tissue culture flasks, vented cap, 25 and 175 cm$^2$ (Costar Corp)
Centrifuge tubes, 15, 50 and 250 ml (Corning)
Sampling site coupler (Baxter/Fenwal, Deerfield, Ill.)
Solution transfer set (Baxter/Fenwal)
Lifecell adapter set (Baxter/Fenwal)
Interconnecting jumper tube, 8" (Gibco)
Solution transfer pump (Baxter/Fenwal)
Culture bags, PL732 1 liter (Baxter/Fenwal)
Culture bags, PL732 3 liter (Baxter/Fenwal)
SBIL-2 retroviral vector (National. Gene Vector Laboratory).
QuickExtract™ DNA extraction solution 1.0 (Epicentre)
First strand cDNA Synthesis Kit (Amersham pharmacia biotech)
STRATAGENE Absolutely RNA™ RT-PCR Miniprep Kit (STRATAGENE)

*Note: 50 Cetus units (CU)=300 International units (IU)

Example 1

This example describes the construction of a retroviral vector comprising and expressing a human IL-2 coding sequence.

The retroviral plasmid IL-2-IRES-eGFP (see, e.g., Liu et al., J. Immunol. 167: 6356-6365 (2001), where eGFP replaces YFP) was used to prepare the retroviral backbone (SB) by digestion with Bam HI, followed by blunt-ending with Klenow fragment and digestion with Not I. The IL-2 cDNA insert vias also prepared from IL-2-IRES-eGFP by digestion with Sal I, followed by blunt-ending with Klenow fragment and digestion with Not I. The resultant insert was directionally cloned into SB. The resultant SBIL-2 vector did not contain any other genes as confirmed by nucleotide sequencing analyses. The construct was then pseudotyped in the packaging cell line PG13, which provided Gibbon Ape Leukemia Virus (GALV) envelope protein. A stable PG13SBIL-2 producer clone was established and genomic analysis revealed that this producer clone contained three copies of the integrated retroviral IL-2 DNA. The vector supernatant produced by this producer clone was shown to be biologically active in transducing a human, non-IL-2-producing, melanoma cell line to produce IL-2 as detected by ELISA.

Example 2

This example describes the generation of gp100-specific, melanoma-reactive, clonal lymphocytes retrovirally transduced with an exogenous IL-2 gene.

Generation of Bulk Cultures:

Complete medium (CM) consists of RPMI 1640 with 25 mM HEPES, pH 7.0, 1 mM Glutamine, 50 U/ml penicillin, 50 micrograms/ml streptomycin, $2 \times 10^{-5}$ M 2-mercaptoethanol, and 10% human AB serum.

PBMCs from patients are obtained 34 weeks after 209-2M immunization by leukopheresis. PBMCs are enriched by centrifugation on lymphocytes medium (LSM), washed two times with HBSS and cryopreserved at $1 \times 10^8$ cells/vial in one ml of human serum (Biowhittaker) with 10% dimethyl sulfoxide (DMSO). PBMCs from normal donors are prepared in a similar fashion.

On day 0, one vial of PBMCs is thawed by warming rapidly to 37° C. Cells are transferred directly into CM. PBMCs are washed twice with CM, and an aliquot is counted. PBMCs ($1.5 \times 10^6$/ml) are plated in each of 4 wells of a 24-well tissue culture plate in 2 ml of CM. 209-2M peptide is diluted 1:1,000 from stock to a final concentration of 1.0 µg/ml (approximately 1.0 micromolar). Plates are incubated at 37° C. in 5% $CO_2$.

On day 1, IL-2 is added to each well to 50 CU/ml final concentration.

On day 4, 1 ml of supernatant is replaced with 1 ml of CM plus 300 IU/ml IL-2. If cell density increases above $2 \times 10^6$ cells/ml, cells are split to half of the density and each new well is fed with 1 ml of CM plus 50 CU/ml IL-2.

Transduction with SBIL-2 Retroviral Supernatant:

On day 6, $2 \times 10^6$ cells from each well are transduced with 8 mls of SBIL-2 retroviral supernatant in Retronectin-coated wells of a 6-well tissue culture plate. Retronectin is coated as follows: 2 mls of 1×PBS containing 50 µg/ml Retronectin is placed in each well of the 6-well plate at 4° C. overnight or at room temperature for 2 hours. Wells are blocked with 2 mls of 1% BSA in 1×PBS at room temperature for 30 minutes and washed once with 2 mls of 1×PBS containing 2.5% HEPES, pH 7.0 (v/v). PBMCs/TILs ($2 \times 10^6$) cell pellet is resuspended with 8 mls of the SBIL-2 retroviral supernatant, and this cell-virus mixture is applied to the Retronectin-coated plate. Cells are exposed to retroviral vector at 37° C. for 6 hours, harvested by centrifugation at 1,000×g for 10 minutes at 4° C., and resuspended again in 8 mls of fresh retroviral supernatant and left in the original Retronectin-coated wells overnight at 37° C. The same transduction procedure is repeated twice on day 7 (total of 4 retroviral exposures in 2 consecutive days). At the end of transduction, cells are washed with CM and resuspended in a cell density of $0.5 \times 10^6$/ml in CM supplemented with 50 CU/ml IL-2.

On day 9, an aliquot of cells is removed from each bulk transduced culture well and assayed for activity. Briefly, $1 \times 10^5$ PBMCs are plated per well of a flat-bottom 96-well tissue culture plate with $1 \times 10^5$ target cells. Typically, six different target cells are tested: T2 cells pulsed with 1.0 µM G280, T2 pulsed with 1.0 µM G209, two HLA-mismatched melanoma cell lines, and two HLA-A2-matched melanoma cell lines. After 24 hours of incubation, supernatants are harvested and IFN-γ is quantified by ELISA capture assay. The well (or wells), which exhibits the most peptide specificity and anti-tumor activity, is selected for cloning.

Cloning from Bulk Cultures:

Active bulk cultures are cloned by limiting dilution in 96-well U-bottom plates. Briefly, allogeneic PBMCs are prepared. PBMCs are obtained by thawing frozen leukopheresis vials from normal donors as described above. PBMCs are thawed directly into CM, washed twice, resuspended in CM, and then irradiated (34 Gy, Nordion gammacell 1000 Cs137 irradiator). Enough cloning reagents for 25 plates are mixed together: 500 ml of CM, $1.25 \times 10^8$ PBMCs, 30 ng/ml OKT3, and 50 CU/ml IL-2. Responder CTL for cloning are prepared by removing an aliquot of PBMCs from the most active bulk culture well, counting the cell number, washing the cells in CM, and resuspending. To 100 ml of the cloning reagent mixture are added 1,000 viable responder cells from bulk culture. These are mixed well and plated in 5 U-bottom plates (2 viable cells/well) using a repeating multichannel pipette. To the remaining 400 ml of cloning reagent mixture are added 1,200 viable cells. These are mixed well and plated in 20 U-bottom plates (0.6 viable cells/well) using a repeating multichannel pipette.

The final components are listed below:

| Component | per well |
|---|---|
| Viable cells | 0.6 or 2.0 |
| Allogeneic PBMCs | $5 \times 10^4$ |
| OKT3 | 30 ng/ml |
| IL-2 | 50 CU/ml |
| CM | 200 µl |

Seven days after plating, 10 CU/well (50 CU/ml) of IL-2 are added to each well.

Fourteen days after plating, wells are screened visually for clonal growth. Growth-positive wells are resuspended by pipetting, and the entire contents of each well is re-plated in a well of a flat-bottom 96-well plate.

Aliquots of all growth-positive wells are tested by coculture assay for specificity and activity. Aliquots (40 µl) of cells from each well are replated in duplicate wells of a 96-well flat-bottom plate. Target cells ($1 \times 10^5$) are added to each well. Typically, one well receives T2 pulsed with G209 and the other well receives T2 pulsed with G280. Alternately, one well receives an HLA-A2 matched tumor and the other well receives an HLA mismatched tumor. Cells are washed by spinning the plates, flicking the contents out of the wells, and applying 150 µl of fresh media to each well. After a 24 hr coincubation period, the supernatants are harvested and IFN-γ secretion is quantified by ELISA. Wells with the highest antigen-specific IFN-γ secretion are identified for further analyses of transduced IL-2 gene by PCR.

Identification of Clones Containing Transduced UL-2 gene:

On day 15 after plating, $1 \times 10^4$ cells from each of clones with highest antigen-specific IFN-γ secretion are subjected to direct DNA PCR analyses with a primer pair of T3 and IL-2 primer 2. T3 primer is specific for retroviral sequences and L-2 primer 2 contains the sequence of the 3' end of the IL-2 gene. Only transduced IL-2 gene will be amplified. Clones that are positive for the transduced EL-2 gene will be chosen for further expansion by REP.

"REP" Expansion of CTL Clones to Therapeutic Numbers:

Each IL-2 transduced tumor-reactive clone is expanded using a single Rapid Expansion Protocol (REP) (Ridell et al., J. Immunol. Methods 128:189 (1990)), then re-tested for activity and specificity. In the first REP, each clonal well is assumed to have approximately $1 \times 10^5$ cells and all cells are used.

Components for the REP mix:

| Component | 25 cm² flask | 150 cm² flask |
|---|---|---|
| viable CTL | $1 \times 10^5$ | $1 \times 10^6$ |
| Allogeneic PBMCs | $2.5 \times 10^7$ | $2 \times 10^8$ |
| OKT3 | 30 ng/ml | 30 ng/ml |
| CM | 25 ml | 75 ml |
| AIM V | | 75 ml |

On day 0 PBMCs are thawed, washed twice, resuspended in CM and irradiated (34 Gy) as described above. PBMC and OKT3 are added to CM, mixed well, and aliquots are transferred to tissue culture flasks. Viable cells are added last. Flasks are incubated upright at 37° C. in 5% $CO_2$.

On day 2 IL-2 is added to 50 CU/ml.

On day 5, 20 ml (130 ml for a 175 cm² flask) of culture supernatant are removed by aspiration (cells are retained on the bottom of the flask). Media are replaced with CM containing 50 CU/ml IL-2.

On day 8 an aliquot of cells is removed for counting and re-assay. Cells are assayed for peptide specificity and tumor recognition by coincubation assay and ELISA. If cell density is greater than $1 \times 10^6$/ml, cells are split into additional flasks or transferred to Baxter 3 liter culture bags. IL-2 is added to 50 CU/ml. Fungizone is added to 1.25 mcg/ml and 1 ml/l Cipro is added.

On day 9, the most active clones are tested for their viability after IL-2 withdrawal. Cells ($2 \times 10^5$) from each clone are washed with CM twice, resuspended in 200 µl CM and plated in wells of 96-well flat-bottom plate. On day 13, cells are assayed for their viability using [3-(4-5-dimethylthiazol-2-yl)-5-(3-carboxymethoxyphenyl)-2-(4-sulfophenyl)-2H-tetrazolium, inner salt] (MTS) assay. The clones with the highest viability are chosen for therapeutic infusion.

On day 11, IL-2 is added to REP flasks at 50 CU/ml. Cells are split if density exceeds $1.5 \times 10^6$ cells/ml.

The most active IL-2 transduced clones are expanded further to therapeutic numbers with additional REP cycles. In these subsequent REP cycles, CTL are counted and the specified number is used (above Table). In the REP cycle immediately preceding infusion, Fungizone and Cipro are added on day 8, and AIM V media is used.

Preparation of the Final Product:

On day 14-20 the final product is prepared for patient infusion. The contents (cells and media) of flasks are transferred to 250 ml centrifuge tubes, while cells in Baxter culture bags are usually harvested using a Baxter/Fenwal continuous centrifuge cell harvester system. Aliquots will be taken from representative bags and pooled for a gram test. Cells will be spun to pellet (1,000 rpm, 15 min, R/T) and combined in a single tube, then washed by resuspension in 0.9% sodium chloride followed by centrifugation, and finally resuspended in 45-150 ml of 0.9% sodium chloride. Human albumin (25%) is added to a final concentration of 2.5%. Aliquots are removed for cell count and viability testing by trypan blue exclusion, and for quality control testing. The final product is then infused intravenously as soon as possible.

Example 3

This example describes the generation of melanoma-reactive, IL-2-transduced TILs.

Multiple TILs cultures derived from tumor fragments and/or digests are set up according to the procedures described in Example 2. TILs are transduced with SBIL-2 retroviral vector with or without REP, depending on their growth rates. A rapidly growing TILs culture is transduced without REP, whereas a slowly growing TILs culture needs a "transduction REP" to stimulate TILs for transduction. All SBIL-2-transduced TILs will undergo a REP to be expanded to the therapeutic number (treatment REP) before they are infused to autologous patients.

Transduction of a Rapidly Growing TIL Culture with SBIL-2 Retroviral Vector:

All transductions are performed in the wells of 24-well plates. Wells are pre-coated with Retronectin followed by SBIL-2 retroviral vector. Retronectin is coated as follows: 2 mls of 1×PBS containing 50 µg/ml retronectin are placed in each well of a 24-well plate at 4° C. overnight or at room temperature for 2 hours. Wells are blocked with 2 mls of 1% human albumin in 1×PBS at room temperature for 30 minutes, and washed once with 2 mls of 1×PBS containing 2.5% HEPES, pH 7.0 (v/v). SBIL-2 retroviral supernatant (2 ml) will be applied to each Retronectin-coated well and incubated at 32° C. for 2 hours followed by 4-16 hours at 4° C. Retroviral supernatant will be removed and 0.5 to $1\times10^6$ TILs in CM supplemented with 1,000 CU/ml IL-2 will be applied onto Retronectin and retroviral vector-coated wells. The culture is incubated at 37° C., 5% $CO_2$ in an incubator overnight. This procedure is repeated daily for four days by transferring the TILs from previous transduction wells to wells freshly coated with SBIL-2 retroviral vector. At the end of transduction, cells are washed and maintained in CM supplemented with 1,000 CU/ml IL-2.

Transduction of Slowly Growing TILs Cultures with SBIL-2 Retroviral Vector (Transduction REP):

Rapid Expansion Protocol (REP):

TILs are expanded in the presence of OKT3 and allogenic feeder PBMCs using an REP as approved by the FDA for use at the Fred Hutchinson Cancer Center (their protocol # 107.00) and at the NCI in protocols 98-C-95 and 99-C-158. In this REP protocol, TILs are stimulated with OKT3 (ORTHOCLONE OKT3®, obtained from commercial sources), irradiated allogeneic feeder cells and IL-2. All components are mixed together in a tissue culture flask, then TILs are added.

| Component | 25 cm² flask | 175 cm² flask |
|---|---|---|
| Viable TILs | $1 \times 10^5$ | $1 \times 10^6$ |
| allogeneic PBMCs | $2.5 \times 10^7$ | $2 \times 10^8$ |
| OKT3 | 30 ng/ml | 30 ng/ml |
| CM | 25 ml | 75 ml |
| AIM V | | 75 ml |

Allogeneic PBMCs are from frozen vials obtained from harvested PBMCs. On day 0, PBMCs are thawed, washed and resuspended in CM, and irradiated. Irradiation of allogeneic cells is performed in an MS Nordion Gammacell 1000, Model 38.3 irradiator, using 5000 rads from a Cs137 source. Testing includes a control culture flask containing only irradiated cells, to verify that they have not proliferated.

On day 2 IL-2 is added to 1,000 CU/ml.

On day 5, 20 ml (130 ml for a 175 cm² flask) of culture supernatant are removed by aspiration (cells are retained on the bottom of the flask). Media are replaced with CM (50% CM/50% AIM V for a 175 cm² flask) containing 1,000 CU/ml IL-2.

Transduction of TIL cells with SBIL-2:

On day 7 after the onset of a REP for TILs, the transduction of replicates of $1\times10^6$ cells are performed in the wells of 6-well plates. Wells are precoated with Retronectin followed by SBIL-2 retroviral vector. Retronectin is coated as follows: 2 mls of 1×PBS containing 50 µg/ml Retronectin is placed in each well of a 6-well plate at 4° C. overnight or at room temperature for 2 hours. Wells are blocked with 2 mls of 1% human albumin in 1×PBS at room temperature for 30 minutes and washed once with 2 mls of 1×PBS containing 2.5% HEPES, pH 7.0 (v/v). SBIL-2 retroviral supernatant (8 ml) is applied to each Retronectin-coated well and incubated at 32° C. for 2 hours followed by 4-24 hours at 4 (C. Retroviral supernatant is removed and $1\times10^6$ TIL cells in CM-supplemented with 1,000 CU/ml IL-2 are applied onto Retronectin and retroviral vector-coated wells. The culture is incubated at 37° C., 5% $CO_2$ overnight. This procedure is repeated on day 8 by transferring the TILs culture from previous transduction wells to the wells freshly coated with SBIL-2 retroviral vector. On day 9, cells are washed and maintained in CM supplemented with IL-2 in a new tissue culture flask. If the cell density increases above $2\times10^6$ cells/ml, cells are split to half of the density and fed within an equal volume of CM plus 1,000 CU/ml IL-2.

Gibbon Ape Leukemia Virus (GALV) Envelope Gene-PCR and $S^+/L^-$ Assays for Replication-Competent Retrovirus (RCR):

SBIL-2-transduced TILs are sent to National Gene Vector Laboratory NGVL) for GALV envelope gene-PCR and S+/L assays to test replication-competent retrovirus (RCR) according to their published methods (Chen et al., Human Gene Therapy 12: 61-70 (2001)). If PCR results are positive and the patient has not been started on chemotherapy, that patient is not treated. In case of a positive RCR PCR for SBIL-2-transduced TIL cells from a patient, who has already received chemotherapy, SBIL-2-transduced TIL cells are not administered. Instead, peripheral blood stem cells collected from the aphereses after G-CSF mobilization prior to the chemotherapy are infused.

Anti-melanoma Activity Assay for the SBIL-2-Transduced and Untransduced TIL Cells:

Briefly, $1\times10^5$ effector cells per well of a flat-bottom 96-well tissue culture plate are coincubated with $1\times10^5$ target cells. Typically, 6 to 8 different target cells are tested, including T2 cells pulsed with 1.0 µg/ml gp100:280-288 or gp100:209-217 peptide or MART 1:27-35 peptide, two HLA-mismatched melanoma cell lines and two HLA-A2 matched melanoma cell lines, and patients' autologous tumor cell lines or frozen tumor cells. After 24 hours of incubation, supernatants are harvested and IFN-γ is quantified by ELISA capture assay. The transduced bulk TILs cultures, which release 200 pg/ml IFN-γ against the autologous tumor or frozen tumor cells, are further expanded.

Detection of the Tranduced SBIL-2 Gene and its Transcript:

Genomic DNA PCR is used to detect the transduced genetic material. A cell pellet of $10^5$ cells (100,000) is resuspended in 1,000 µl of QuickExtract™DNA extraction solution 1.0. Ten microliters of this solution containing 1,000-cell-equivalent DNA are subjected to PCR reaction containing IL-2 Primer 1 (5'GGAGGCCTGGATCCATG-TACAGGATGCAACTCCT 3' [SEQ ID NO: 1]) and Primer 17 (5'CTTCTTGGGCATGTAAAACT 3' [SEQ ID NO: 2]). The PCR products are fractionated on a 2% agarose gel. The presence of a 221-bp fragment, not present in untransduced cells, is defined as positive.

The transduced IL-2 gene expression is evaluated by RT-PCR. Transduced cells ($1\times10^6$) are used for RNA extraction using STRATAGENE Absolutely RNA™ RT-PCR Miniprep Kit. The total RNA is subjected to firs-strand cDNA synthesis by Amersham Pharmacia Biotech Kit. The first-strand cDNA is subjected to PCR reaction containing Primer 16 (5'GTCAGCGGGGGGTCTTTCATT3' [SEQ ID NO: 3]) and Primer 2 (5'GGGTCGACGGATCCTCAAGT-TAGGTTGAGATGA3' [SEQ ID NO: 4]). The PCR products are fractionated on a 1% agarose gel. The presence of an 885-bp fragment, not present in untransduced cells, is defined as positive for SBIL-2 vector-derived IL-2 mRNA transcript.

"REP" Expansion of SBIL-2 Transduced TILs to Therapeutic Numbers:

SBIL-2-transduced TILs are expanded using a single REP, then re-tested for activity and specificity according to the protocol as described above. Eight days prior to cell harvest and re-infusion, an aliquot of cells is removed for counting and re-assay. Cells are assayed for peptide specificity and tumor recognition by co-incubation assay and ELISA as described above. If cell density is greater than $1\times10^6$/ml, cells are split into additional flasks or transferred to Baxter 3 liter culture bags. IL-2 is added to 1,000 CU/ml. Fungizone is added to 1.25 mcg/ml and Cipro is added to 5-10 mcg/ml. On day 11, IL-2 is added to REP flasks at 1,000 CU/ml. Cell cultures are split as needed.

On day 14, cells are harvested and either prepared for additional REP cycles or cryopreserved. If cells have grown to sufficient numbers for patient treatment, a sample is collected from each flask for microbiology tests 2-3 days before the beginning of TIL therapy (the test takes 2 days). IL-2 is added to 1,000 CU/ml on day 14 and every 3 days until the final product is prepared for infusion.

Preparation and Testing of the Final Product:

On day 12-20 the final product is prepared for patient infusion. The contents (cells and media) of flasks are transferred to 250 ml centrifuge tubes, while cells in Baxter culture bags are usually harvested using a Baxter/Fenwal continuous centrifuge cell harvester system. Aliquots are taken from representative bags and pooled for a gram test. Cells are spun to pellet (1,000 rpm, 15 min, RJT) and combined in a single tube, then washed by resuspension in 0.9% sodium chloride, followed by centrifugation, and finally resuspended in 45-400 ml of 0.9% sodium chloride. Human albumin (25%) is added to a final concentration of 2.5%. Aliquots are removed for cell count and viability testing by trypan blue exclusion, and for quality control testing. The final product is infused intravenously as soon as possible.

All references; including publications, patent applications, and patents, cited herein are hereby incorporated by reference to the same extent as if each reference were individually and specifically indicated to be incorporated by reference aid were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, aid the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of preparing autologous T-lymphocytes for re-introduction into a patient having cancer, which method comprises:
   (i) obtaining peripheral blood mononuclear cells (PBMCs) from a patient immunized with an antigen of the cancer,
   (ii) stimulating the PBMCs with the antigen of the cancer in vitro, and
   (iii) transducing the PBMCs with a retroviral vector, which (a) comprises and expresses a human interleukin-2 (IL-2) coding sequence operably linked to a retroviral promoter, (b) does not comprise an exogenously introduced gene that enables phenotypic selection, and (c) comprises a viral envelope that efficiently transduces CD8+ T-lymphocytes,
   whereupon autologous T-lymphocytes are prepared for re-introduction into a patient having cancer.

2. The method of claim 1, wherein the cancer is melanoma.

3. The method of claim 2, wherein the antigen of the cancer is gp100.

4. The method of claim 3, wherein the antigen is the 209-2M peptide (SEQ ID NO: 5).

5. The method of claim 1, wherein the cancer is breast cancer.

6. The method of claim 5, wherein the antigen of the cancer is Her-2/Neu.

7. The method of claim 1, wherein the cancer is prostate cancer.

8. The method of claim 7, wherein the antigen of the cancer is prostate-specific antigen (PSA).

9. The method of claim 1, wherein the cancer is colon cancer.

10. The method of claim 9, wherein the antigen of the cancer is carcinoembryonic antigen (CEA).

11. The method of claim 1, wherein the viral envelope protein is Gibbon ape leukemia virus envelope (GALV).

12. The method of claim 1, wherein the retroviral vector further comprises and expresses a human IL-2 receptor α-chain coding sequence.

13. The method of claim 1, wherein the method further comprises introducing into the PBMCs a vector comprising and expressing a human IL-2 receptor α-chain coding sequence operably linked to a promoter.

* * * * *

SEQUENCE LISTING

<160> NUMBER OF SEQ ID NOS: 5

<210> SEQ ID NO 1
<211> LENGTH: 34
<212> TYPE: DNA
<213> ORGANISM: Artificial Sequence
<220> FEATURE:
<223> OTHER INFORMATION: Synthetic

<400> SEQUENCE: 1
ggaggcctgg atccatgtac aggatgcaac tcct          34

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
cttcttgggc atgtaaaact          20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
gtcagcgggg gtctttcatt          20

<210> SEQ ID NO 4
<211> LENGTH: 34
<212> TYPE: DNA

```
<213> ORGANISM: Artificial Sequence
<220> FEATURE:
<223> OTHER INFORMATION: Synthetic

<400> SEQUENCE: 4
gggtcgacgg atcctcaagt tagtgttgag atga                                    34

<210> SEQ ID NO 5
<211> LENGTH: 9
<212> TYPE: PRT
<213> ORGANISM: Artificial
<220> FEATURE:
<223> OTHER INFORMATION: Synthetic

<400> SEQUENCE: 5

Ile Met Asp Gln Val Pro Phe Ser Val
1               5
```